US009571166B2

(12) United States Patent
Metzenthen

(10) Patent No.: US 9,571,166 B2
(45) Date of Patent: Feb. 14, 2017

(54) TESTING TUNED CIRCUITS

(75) Inventor: Bill Metzenthen, Ormond (AU)

(73) Assignee: Cochlear Limited, Macquarie Univeristy, NSW (AU)

( * ) Notice: Subject to any disclaimer, the term of this patent is extended or adjusted under 35 U.S.C. 154(b) by 1245 days.

(21) Appl. No.: 13/553,798

(22) Filed: Jul. 19, 2012

(65) Prior Publication Data
US 2014/0024919 A1 Jan. 23, 2014

(51) Int. Cl.
*G01R 27/04* (2006.01)
*A61B 5/05* (2006.01)
*H04B 5/00* (2006.01)
*A61B 5/00* (2006.01)
*A61B 5/107* (2006.01)
*A61N 1/372* (2006.01)
*A61N 1/36* (2006.01)
*H04R 25/00* (2006.01)

(52) U.S. Cl.
CPC .......... *H04B 5/0075* (2013.01); *A61B 5/0031* (2013.01); *A61B 5/1075* (2013.01); *A61N 1/37223* (2013.01); *A61N 1/37252* (2013.01); *A61B 2560/0219* (2013.01); *A61B 2560/0271* (2013.01); *A61B 2562/0223* (2013.01); *A61B 2562/046* (2013.01); *A61N 1/36032* (2013.01); *H04R 25/606* (2013.01)

(58) Field of Classification Search
None
See application file for complete search history.

(56) References Cited

U.S. PATENT DOCUMENTS 8,072,310 B1 * 12/2011 Everhart .............. H04B 5/0043
340/10.1
2013/0043888 A1 * 2/2013 Soar ........................ F41H 1/02
324/655

OTHER PUBLICATIONS

Printout of http://www.graphpad.com/guides/prism/6/curve-fitting/reg_damped_sine_wave.htm accessed Jan. 5, 2016.*
Printout of https://en.wikipedia.org/wiki/Damped_sine_wave accessed Jan. 5, 2016.*

* cited by examiner

*Primary Examiner* — Long V Le
*Assistant Examiner* — Bradley Impink

(57) ABSTRACT

Methods and systems for determining one or more parameters of a tuned circuit forming part of a wireless energy transmission system in an implanted (or implantable) medical device are described. The method involves energizing the tuned circuit then receiving a signal back from it. This signal is then analyzed to determine a property of the circuit such as its quality factor (Q) or resonant frequency. Also described herein is a method and system for determining the implantation depth of a component of an implanted medical device. The method involves determining the position of a magnetic element which is mounted in a fixed physical relationship with the component of the medical device. The methods can be performed on an implanted medical device without the need to explant the device.

23 Claims, 11 Drawing Sheets

TESTING TUNED CIRCUITS

BACKGROUND

Field of the Invention

The present technology relates generally to the testing of an aspect of, an implantable medical device. In one form, a parameter of a tuned circuit forming part of an implantable medical device is tested. In another, a location of a part of an implantable medical device is tested.

Related Art

Implantable medical devices are used to assist recipients with a wide range of conditions including sensory, motor or cognitive conditions. One group of implantable medical devices are auditory prostheses, such as middle ear implants, cochlear implants, brain stem implants, auditory mid-brain implant and other devices which provide acoustic, mechanical and/or electrical stimulation to a recipient to assist with hearing. Many implantable medical devices include an internal unit which is implanted in a recipient and an external unit which performs energy-consumption intensive processing or other functions that must be performed outside the body. In such systems there is a requirement for energy (power) and/or data to be delivered transcutaneously from the external unit to the implanted unit. This is generally performed wirelessly, as a physical link between the external and internal units may cause discomfort to the recipient and may be a potential source of infection.

To illustrate transcutaneous wireless inductive energy transmission FIG. 1 illustrates a schematic block diagram of an implantable cochlear implant system 1. The system 1 includes an external unit 3 having a microphone 7, a sound processor 8 and a radio frequency (RF) transmitter 10. The system 1 is powered by a battery 9 that is located in the external unit 3. Since the external unit 3 is typically worn behind the recipient's ear, there is a constraint on the size and weight of the external unit 3 and consequently there is a need for efficient usage of the power of the battery 9.

In order to transmit energy to the internal unit 5, the external unit 3 is provided with an external coil 11 that is coupled to a radio frequency transmitter 10. The transmitter 10 generates a radio frequency alternating in current in coil 11, which generates an oscillating magnetic field. That field extends through the recipient's skin 13 and interacts with an implanted coil 17 that is located so as to enable inductive coupling with the external coil 11. The received signal is induces an EMF in the implanted coil 17 of the implanted unit 5 of the system 1. A signal 16 may also be transmitted from the implanted unit 5 to the external unit 3, for example to provide telemetry about the status of the implanted unit 5.

Generally speaking, the implanted unit 5 includes: circuitry 19 that rectifies and regulates the received RF signal 15; a data decoder 21 that extracts the data encoded in the received RF signal 15; and an amplifier 23 that drives an actuator 25 based on the decoded data. The actuator may, for example, include an array of electrodes that stimulate the auditory nerve of the cochlea of the recipient to give a sensation of sound (also referred to as a 'sound percept'). FIG. 2 illustrates a simplified circuit diagram of components involved in the transfer of electrical energy from the external unit 3 to the implanted unit 5.

The RF transmitter 10 is part of the external unit 3 and connects an RF source 12 (in commercially available cochlear implant systems, e.g., from Cochlear Limited, Sydney Australia, the RF source operates, e.g., at a frequency of 5 MHz) to the transmitter coil 11.

The separation distance, d, between the coils 11 and 17, which are typically positioned with their centres on a common axis, is determined by the depth at which the internal coil 17 is implanted in the recipient's body. This depth is sometimes known as the skin flap thickness (SFT), as the implantation depth is determined by the thickness of the flap of skin overlying the coil 17. In practice, the SFT may be in the range, e.g., from about 0 mm to about 12 mm, but is preferably as low as safely possible in order to maximise efficiency of coupling between the external coil 11 and the internal coil 17. The separation distance d affects the transfer of electrical energy to the implant (link efficiency) and modulates the electrical voltage that is generated in the implant electronics. However, typically the separation distance d is not accurately known.

The internal coil 17 forms part of a tuned (resonant) circuit 101 along with a tuning capacitor 130. Electrical energy to sustain the device's functionality is extracted from the tuned circuit 101 by rectifying the received RF signal, using a transformer 100 and a rectifier diode 102, and storing the received electrical energy in a storage capacitor 104. The voltage across the storage capacitor is denoted is the implanted unit's supply voltage 107. A primary voltage protection diode 106 is provided to shunt excess voltages, that might be generated by external sources, to a level that is considered safe for the operation of the implant electronics. Additional circuitry for protecting the electronics can also be provided.

The supply voltage 107 provides energy to an electrical load 120, which includes a data decoder 21, an amplifier 23 and an actuator 25.

A factor in prolonging battery life in the external unit 3 is the efficiency of coupling between the external coil 11 and the tuned circuit 101 of the internal unit 3. However, even if the initial coupling of the RF link in an implanted medical device is good at implantation, the properties of the circuit may drift over time, leading to reduced efficiency.

For example, over time the properties of the metal from which the implanted coil 17 is made can change. Moreover, the bodily environment in which the implanted coil 17 resides is harsh, and in some situations if the sealing of the implanted coil 17 breaks down, the implanted coil 17 may be exposed to bodily fluids and tissues, which can cause further performance degradation. In some instances, the implanted coil 17 or its connections to other components of the tuned circuit 101 can fail mechanically. This could be caused, e.g., by a bump or knock on the body part on which the coil 17 is mounted.

SUMMARY

Embodiments of the present technology are directed to methods and systems for determining one or more parameters of a tuned circuit forming part of a wireless energy transmission system in an implanted (or implantable) medical device. Such methods include energising the tuned circuit then receiving a signal back from it. This signal is then analysed to determine a property of the circuit such as its quality factor (Q) or resonant frequency. Such embodiments can be advantageously employed prior to implantation, e.g. during manufacture or testing.

Other embodiments of the present technology are directed to a method and system for determining the implantation depth, d, of a component of an implanted medical device. Such a method includes determining the position of a magnetic element which is mounted in a fixed physical relationship with the component of the medical device. For example, the component being analysed is a coil of a tuned circuit forming part of the wireless energy transmission system of the implanted medical device.

Such systems can be integrated into a common test unit, respectively.

Advantageously, these methods can be performed on an implanted medical device in vivo, i.e., without the need to explant the device.

BRIEF DESCRIPTION OF THE DRAWINGS

Illustrative embodiments of the present technology are described below by way of non-limiting example with reference to the accompanying drawings, in which.

DETAILED DESCRIPTION

In the course of developing embodiments of the present technology, the inventor: observed: from time to time, in a clinical setting, a recipient of an implanted medical device may report a problem with the implant for which the cause may be related to the RF link of a recipient's implant system; accordingly, knowledge of the properties of a recipient's implant, and particularly its energy transmission system, then is of particular interest to recipients, clinicians, implanted medical device manufacturers and designers; and to date, however, no mechanism has existed to test the properties of the implanted unit's tuned circuit such that a need exists for the same. At least one embodiment of the present technology, among other things, addresses the need recognized herein by the inventor.

A system for testing a tuned circuit of an implantable medical device will now be described. The tuned circuit to be tested has a coil for transferring energy between it and another inductively coupled coil of the medical device. The system includes: a field generator to induce an electromotive force (EMF) in the coil of the tuned circuit; a field detector to detect resonance of the tuned circuit; and an analysis system to analyse the detected resonance over a period of time to determine a property of the tuned circuit. The field generator can be a signal generator coupled to a radiating coil configured to emit an oscillating magnetic field when energised by a signal generated by the signal generator. The field detector may also include a coil arranged to interact with a field produced by the resonating tuned circuit. This may be the same coil that is a part of the field generator. The detector can also include a digitiser to convert an analog output of the coil to a digital signal for analysis.

Figure 3:
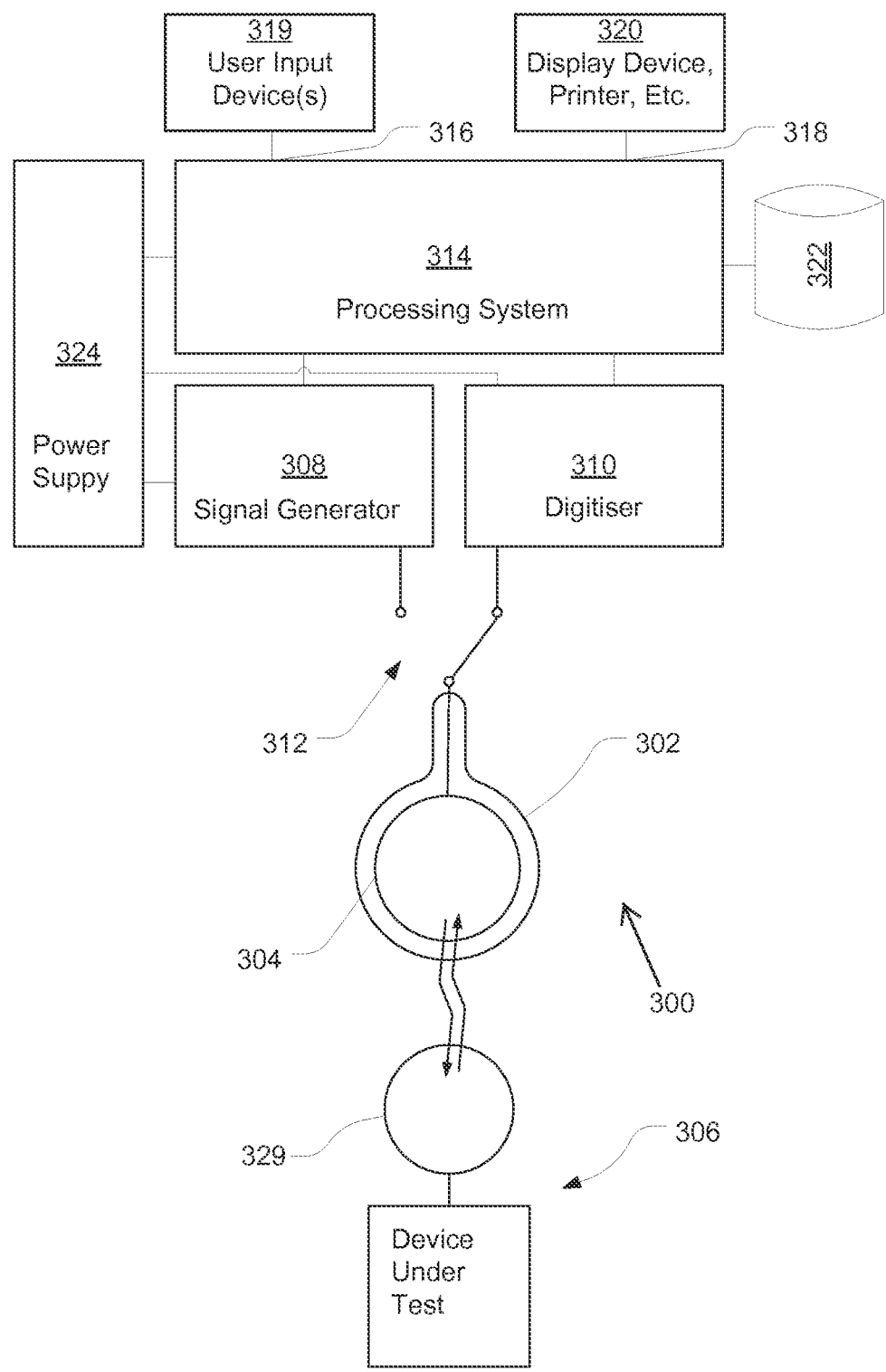
FIG. 3 is a schematic block diagram illustrating components of a tuned circuit testing system according to another embodiment of the present technology.
Figure 4:
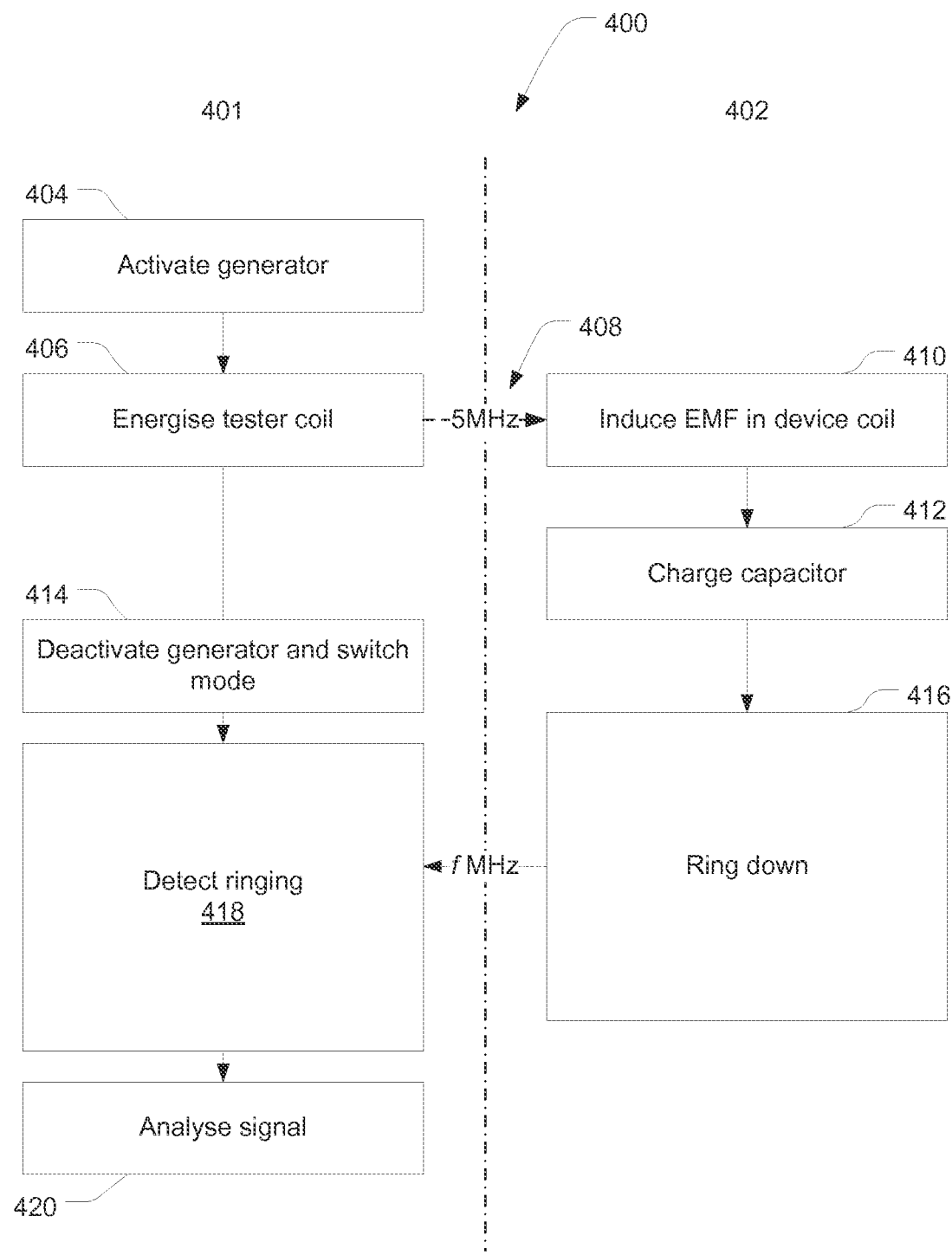
FIG. 4 is a flow diagram illustrating a method of operation for testing performance of tuned circuit according to another embodiment of the present technology.

FIG. 3 is a schematic block diagram illustrating components of a tuned circuit testing system 300 according to an embodiment of the present technology. And FIG. 4 is a flow diagram illustrating a method 400 of operation for testing performance of tuned circuit, according to an embodiment of the present technology. The tuned circuit testing system 300 of FIG. 3, and the associated flow diagram of, FIG. 4 describe can be used for measuring one or more properties of a tuned circuit in an implanted (or implantable) medical device. The example will be described in the context of performing in vivo testing of the tuned circuit. However, in other embodiments a similar testing methodology and system could be used to test the tuned circuit of an implantable medical device either during manufacture or prior to implantation, to verify correct operation of the tuned circuit and/or to determine the baseline characteristics of the circuit prior to implantation.

In FIG. 3, the tuned circuit testing system 300 includes a probe 302 which houses a test coil 304. The test coil 304 is used to inductively couple the testing system 300 with a tuned circuit of a device under test 306. The coil 304 is arranged for selective connection to a signal generator 308 or a digitiser 310 via a switch 312.

The signal generator 308 outputs an alternating current of a desired frequency. In the illustrative example, the generator outputs a signal at 5 MHz, although other frequencies may be used in other embodiments of the present technology, depending on the likely resonant frequency of the device under test 306.

The digitiser 310, e.g., includes a high speed analogue to digital converter that receives an analogue input from the coil 304 and outputs a digital signal for further analysis.

The selective connection of the coil 304 of the probe 302 to either the generator 308 or digitiser 310 is performed via the switch 312, which may be selectively switched between connection to the generator and digitiser as required in the method to be described below.

Operation of the tuned circuit testing system 300 is controlled by a data processing system 314. The data processing system 314 for example can be a general purpose computer, including one or more processors that are programmed to perform a method, e.g., as described in connection with FIG. 4. The processing system 314 includes an input/output port 316 and output port 318 in communication with external devices. In this example, the input/output port 316 may be connected to one or more user input devices 319, e.g., a keyboard and/or mouse, in order to allow the operator of the system 300 to enter details about the device under test 306, its recipient or other details which may be needed by the system or desirable to track in the testing process. A display, printer or other output device 320 is connected to the input/output port 318 in order to provide an indication of operation of the device to its user. As will be appreciated, in some instances the input and display components may be integrated into single device, such a touch screen device which performs both input and output functions.

The data processing system 314 is also connected to a memory system 322 which will include both program data and working data which is used by the processor to execute the methods described herein. The memory 322 can also include data storage, e.g. a hard drive or solid state disk or the like, which is used to store test data and test outputs for later use or further processing.

Each of the components is supplied with energy (power) from a power supply 324. It will be appreciated that in the event that the system 300 is used for in vivo testing, and if the system is powered from the electrical mains, then the power supply will need to comply with safety requirements for power supplies used for medical devices in order to ensure safety for the recipient whose device is being tested and the operator of the system. Alternatively, a battery can be used to supply the system.

One possible embodiment of the system 300 is to incorporate all of the components of the system 300 into the casing of the probe 302.

In the flow diagram of FIG. 4, the left hand column 401 illustrates the steps performed by the test system 300 and the right column 402 illustrates the operation (the intended induced response) of the device under test 306.

Prior to beginning the process 400, the user of the system 300 is required to position the probe 302 such that its coil 304 is substantially aligned with the induction coil 329 of the device under test 306. As described below, an initial alignment process can also be performed.

The process begins in block 404 by connecting the test coil 304 to the generator 308 via switch 312. At block 406, the device under test 306 energises the testing coil 304 with a high frequency AC voltage. As noted above, e.g., a frequency of about 5 MHz is suitable in some applications. When the testing coil 304 is energised with the radio frequency signal, the coil 304 of the testing system 300 generates a magnetic field oscillating at the generator's output frequency. In this example, a 5 MHz oscillating magnetic field is produced. The magnetic field 408 intersects the coil 329 of the device under test 306 and in block 410 induces a time varying EMF in the coil 329. The induced EMF in the coil 329 charges the tuning capacitor 130 (as well as the storage capacitor 104) of the device under test 306 to store energy in the tuned circuit at block 412.

Next, at block 414, the generator 308 is deactivated and the switch 312 configured such that the coil 304 of the probe 302 is connected to the digitiser 310. In this mode, no additional energy is coupled into the coil 329 of the device under test 306. However, the tuned circuit of the device under test 306 will "ring" and expend its stored energy, radiating it via the coil 329. This is indicated in block 416. During this "ring down" phase, the amount of energy in the output signal from the coil 329 diminishes over time. The oscillating electrical signal in the coil 329 will generate an oscillating magnetic field having a frequency, f, which will interact with the coil 304 of the test system 300 and induce an alternating EMF therein. In block 418, the induced EMF in the coil 304 is detected and digitised by the digitiser 310. The digitiser 310 samples the time varying output of the coil 304 and the digitised output signal is then passed to the processing system 314 for analysis in block 420. For example, the method 400 is iterative, and so can be repeated a number of times and the results averaged to cancel noise before the analysis in block 420.

According to one embodiment of the present technology, in block 420, the received digitised signals are analysed to determine the frequency of the oscillation of the tuned circuit of the device under test 306 and the quality factor (Q) of the tuned circuit of the device under test 306.

In an initial phase, an alignment process can be performed to assist the user of the testing system to achieve correct alignment of the test coil 304 and the induction coil 329 of the device under test 306. The alignment process essentially involves repeating the process 400 while monitoring the received signal amplitude. This allows the signal level received by the digitiser 310 to be maximised (or at least substantially maximised). The system can facilitate the identification of the correct alignment by cycling through the process 400 and providing a real-time display of the voltage amplitude of the signal received by the digitiser 310 to the user, while the user attempts to align the coils 304 and 329. In this initial alignment phase, a reduced level of signal analysis may be used, since only the signal amplitude is necessary for determining the quality of alignment.

Figure 5:
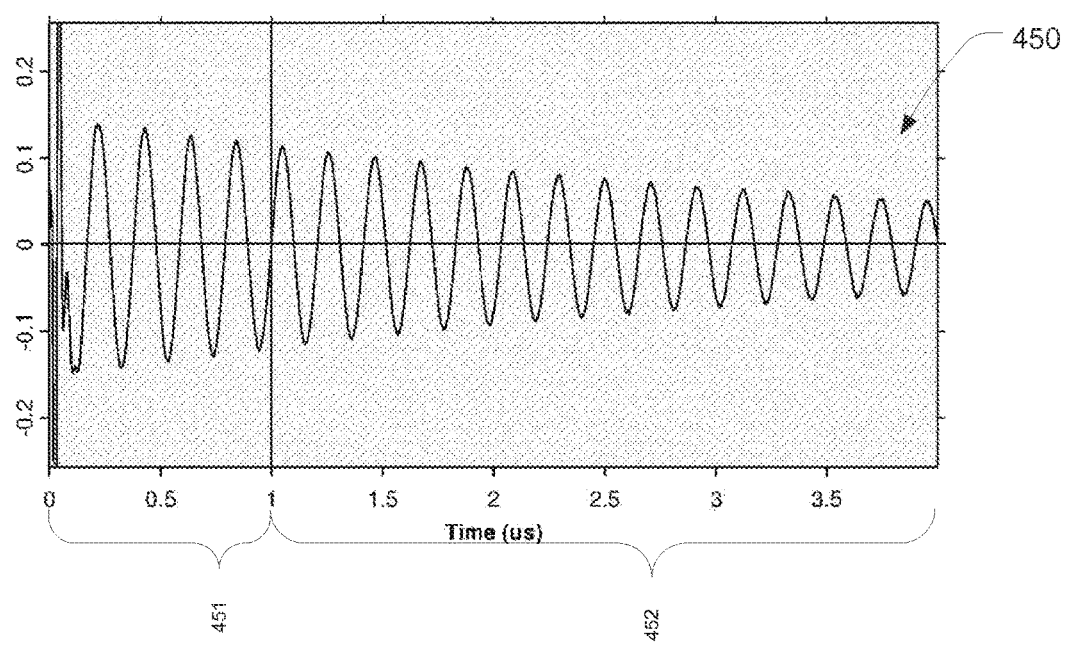
FIG. 5 is an exemplary output from a measurement made using a probe of the system of FIG. 3.

FIG. 5 illustrates an exemplary output signal produced by the digitiser 310 of the system 300. The plot 450 illustrates the digitiser output signal over a 5 microsecond period beginning at time to 0, when the input from the coil 304 is switched into the digitiser 310.

It can be advantageous to collect several waveforms, for example one hundred, and process them, e.g., take their average, in order to reduce the effects of unrelated noise upon the measurement. Since the measurement time of the method 400 is short, this has only a small impact upon the total time taken to perform a measurement.

Over an initial period/window 451, e.g., typically less than 1 microsecond, the output from the coil 304 to the digitiser 310 includes large amounts of unwanted signals. In the time period/window 451, the output of the digitiser 310 is discarded. Analysis of the digitiser 310 output begins at the start of a measurement window 452 that follows period/window 451. In this example, the measurement window 452 is begun at about 1 microsecond, although in some embodiments the measurement window may start at an earlier time, e.g., 400 nanoseconds after measurement begins.

As can be seen, the output of the digitiser in the measurement window 452 is a decaying sinusoidal form. The digitised signal in the measurement window 452 is analysed by the processing system 314 to find a best fit function. In its simplest form, the curve fitted to the digitised signal is of the form:

$$v = Ve^{-\frac{t}{\tau}}\sin(2\pi f t + \phi)$$

where: v is the voltage of the output signal output at time t; V is an initial voltage amplitude at a start of the measurement window; τ is a decay constant describing the energy dissipated in a cycle of the received signal compared to the total signal energy; f is the resonant frequency of the tuned circuit; and ϕ is a phase offset.

Well known methods such as those using least squares and conjugate directions may be used as the basis of a method for finding the fitted curve. On such method, e.g., is described by Powell ("An efficient method for finding the minimum of a function of several variables without calculating derivatives", The Computer Journal, Vol 7, p. 155).

Once the curve is fitted, the resonant frequency of the tuned circuit of the device under test 306 is then given by f (as per the equation above) and the quality factor (Q) is determined using:

$$Q=\pi f\tau.$$

In practice, a more complex function may need to be used in order to compensate for defects in the equipment and/or measure more complex behaviour of the tuned circuit.

For example the curved fitted to the output voltage values can include additional terms as follows:

$$v = Ve^{-\frac{t}{\tau}}\sin(2\pi ft + \phi) + a + bt$$

where a and b represent noise and imperfections in the digitiser 310. The term bt introduces a dc shift, so the simple form bt can be replaced by the alternative expression:

$$b\left(1 - \frac{2t}{T}\right)$$

where T is the measurement window.

In some cases, non-linearity in the tuned circuit can cause the frequency f to vary with time (i.e., to chirp). This can be approximated by replacing f with a function of time, such as:

$$f_0 + tf_1 + t^2 f_2 + \ldots$$

Similarly, non linearity in the elements of the tuned circuit can cause the decay of the resonant signal to depart from a strictly exponential form. This can be approximated by replacing $$Ve^{-\frac{t}{\tau}}$$

with a function such as:

$$V_0 e^{-\frac{t}{\tau}} + V_1 e^{-\frac{2t}{\tau}} + V_2 e^{-\frac{3t}{\tau}} + \ldots .$$

Moreover, some tuned circuits have more than one resonance. A similar process can be used to find the properties of the multiple resonances, for example, by replacing the decaying sinusoid with the sum of two (or more) decaying sinusoids. Alternatively, an iterative approach to fitting the curve can be adopted where the residue from an earlier curve fitting process is used as the raw data for another round of fitting. This can be repeated more than once if necessary.

Advantageously, using the method and apparatus of FIGS. 3 and 4, interrogation and testing of an implanted tuned circuit forming part of the energy transmission link in an implanted medical device can be performed, without the need for physical connection between the circuit under test and the testing equipment. As will be appreciated, the technique described herein only requires a short period of time to perform. In principle, the technique only requires, e.g., microseconds to perform. However, the computational analysis may take, e.g., several hundred milliseconds on an ordinary desktop computer. The time taken to perform the test may be further increased by the need to charge the storage capacitor 104 to at least some minimum level prior to moving into the detection phase of the measurement. But overall, the process may take less than, e.g., one second to test the function of the resonant circuit. This speed of testing also makes such a process viable for integration into a manufacturing process, or quality checking process, for the coil or implantable medical device.

A system for determining a position of a component of an implanted medical device will now be described. The component for which the position is to be located includes a magnetic element positioned in a fixed spatial arrangement with respect thereto. The system includes: one or more sensors for detecting a localised magnetic field produced by the magnetic element at a plurality of positions remote from the component; a processor to compare the measured localised magnetic field at a plurality of said remote positions with a model of the magnetic field produced by the magnetic element; and to thereby determine the position of the magnetic element with respect to the plurality of locations. The model of the magnetic field produced by the magnetic element can be stored in a memory, e.g., in a look up table, that can be interrogated by the processor to determine a relative position of the one or more sensors and the magnetic element at a point in time. The one or more sensors can include a plurality of Hall effect sensors. If a plurality of Hall effect sensors is used, these can be mounted in a fixed spatial relationship with one another, e.g. in a hand held probe, and used to determine a set of magnetic field readings in a set of positions in a known spatial relationship with each other. In an embodiment with a probe of this type, the probe can include indicia to selectively indicate correct alignment of the probe relative to the device being tested.

Figure 1:
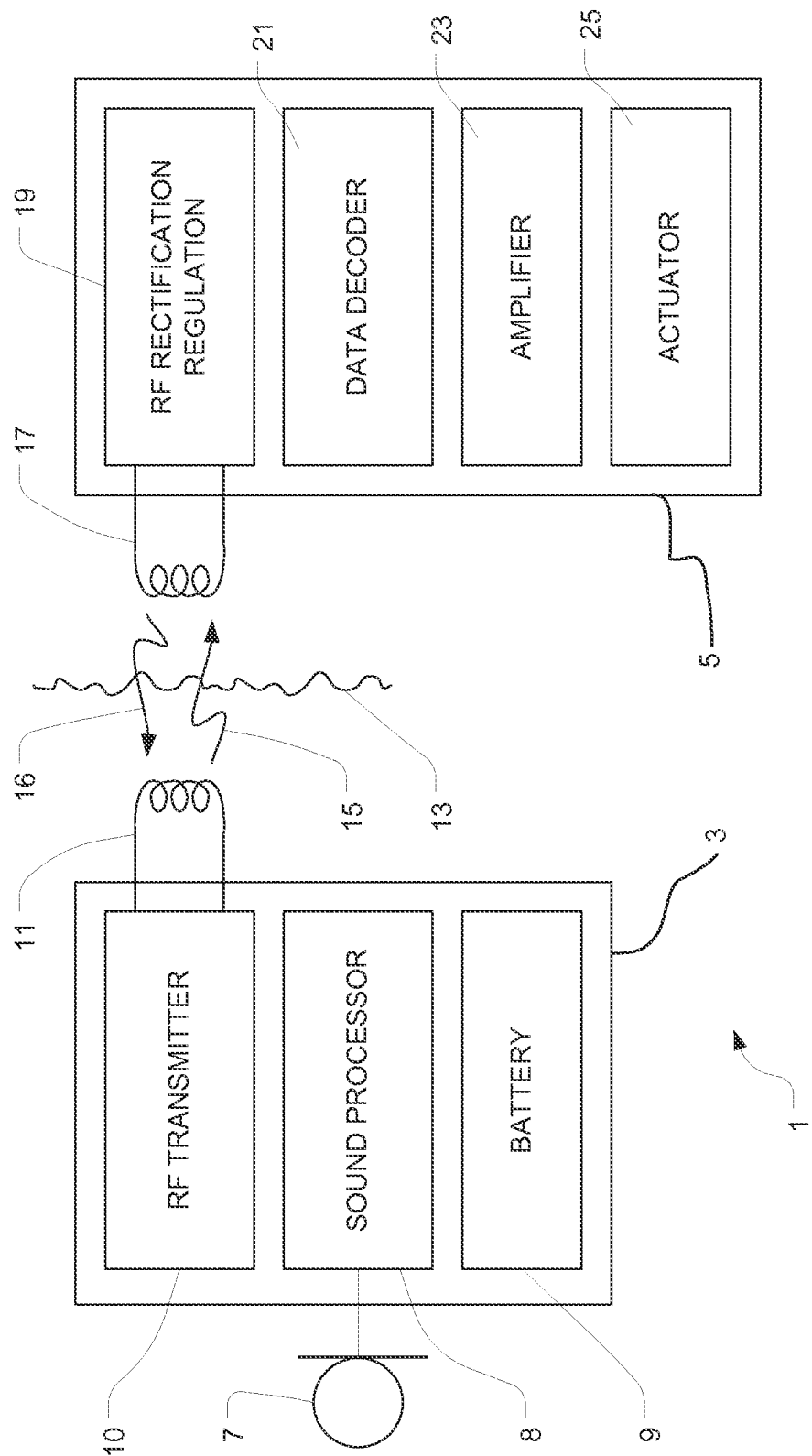
FIG. 1 is a schematic block diagram of a cochlear implant system.
Figure 2:
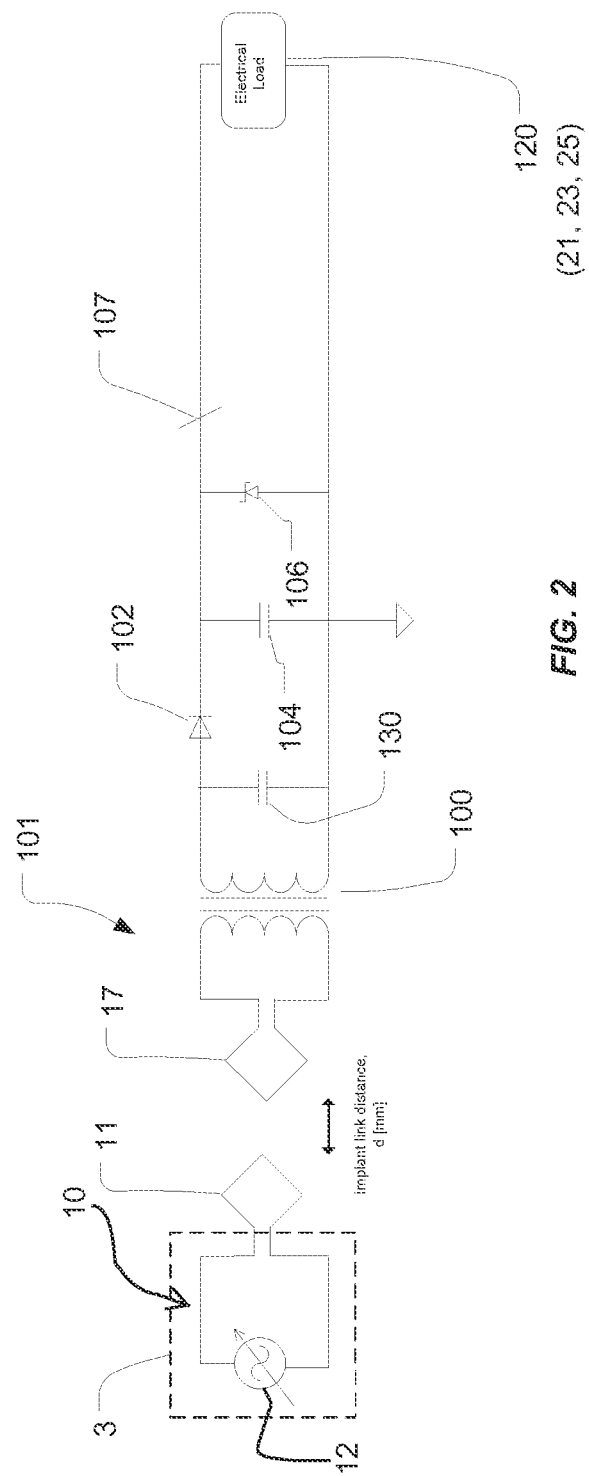
FIG. 2 is a schematic diagram of the transcutaneous energy transmission system of FIG. 1.
Figures 6A, 6B:
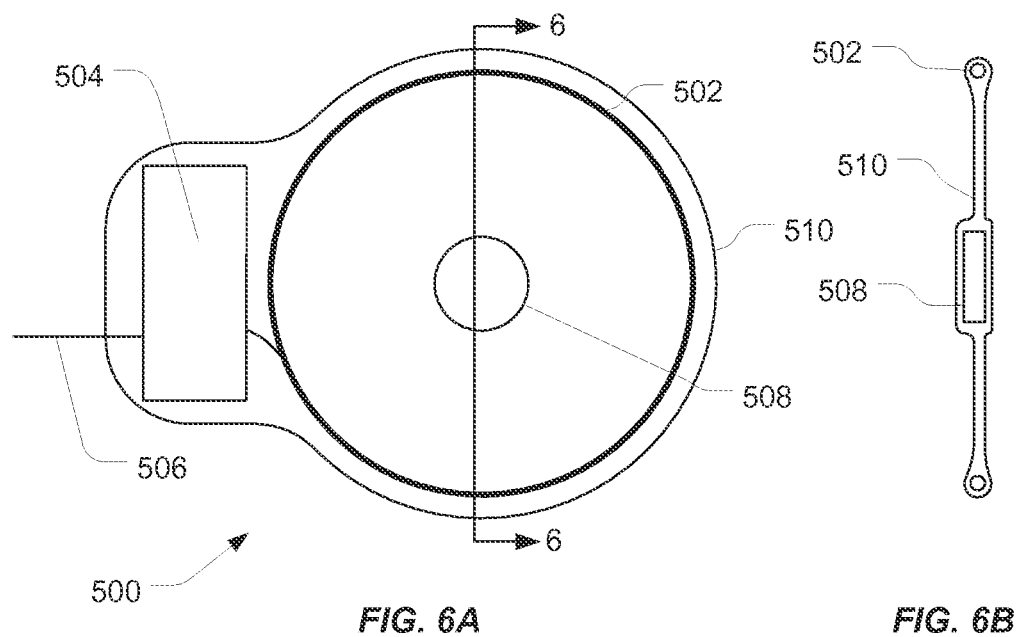
FIG. 6A is a schematic representation of an implantable unit of a medical device, according to another embodiment of the present technology, which includes an induction coil forming part of a resonant circuit and a magnetic element.
FIG. 6B is a cross-sectional view along lines 6-6 of FIG. 6A.

FIG. 6A illustrates an implantable unit 500 of an implantable medical device, e.g., a cochlear implant, according to another embodiment of the present technology. The implantable unit 500 includes an energy transmission coil 502 which is connected to device electronics 504. The device electronics 504 comprise, e.g., the RF rectification regulation subsystem 19, data decoder 21, amplifier 23 and actuator 25 of the internal unit 5 of the device 1 described above in connection with FIG. 1. The actuator 506, in this example, is a lead housing an array of one or more electrodes for applying stimulation to the auditory nerve of the recipient. Concentrically mounted with the energy transmission coil 502 is a magnetic element 508. The implantable unit 500 is encased in a suitable housing material 510 to provide protection once implanted. The magnetic element 508 is held by the casing 510 in a fixed physical relationship with the coil 502. In use, the magnetic element 508 is used to hold the external coil of the wireless energy transmission link, e.g., coil 11 in FIGS. 1 and 2, in alignment with the coil 502.

Figure 7:
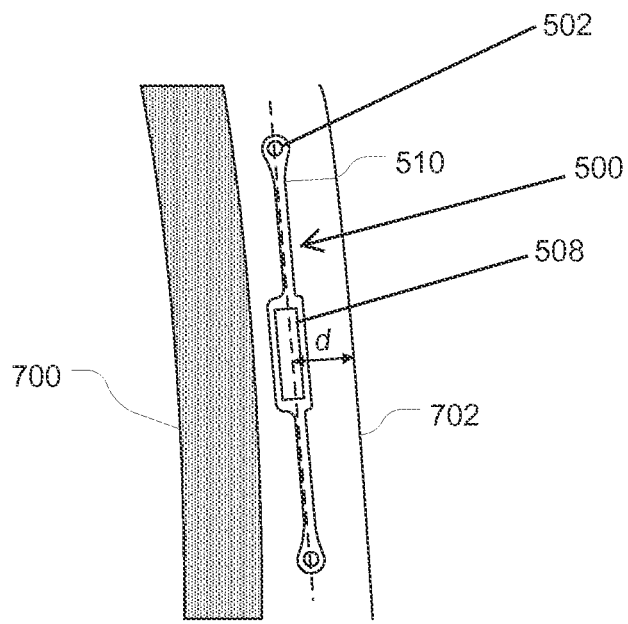
FIG. 7 illustrates the implanted device of FIGS. 6 and 6A implanted at a depth d beneath the skin surface of recipient.

FIG. 6B illustrates a cross-sectional view of the implanted unit 500 taken along line 6-6 of FIG. 6A. As can be seen, the centrally located magnetic element 508 sits in a generally planar relationship with the coil 502 and is encased in the housing material 510. FIG. 7 illustrates the device 500 implanted in a recipient. The implanted device 500 is mounted between a bone, e.g., skull, 700 and a skin surface 702. The depth of implantation of the device 500 beneath the skin surface 702 is denoted by d. This depth is also known as the skin flap thickness.

Figure 8:
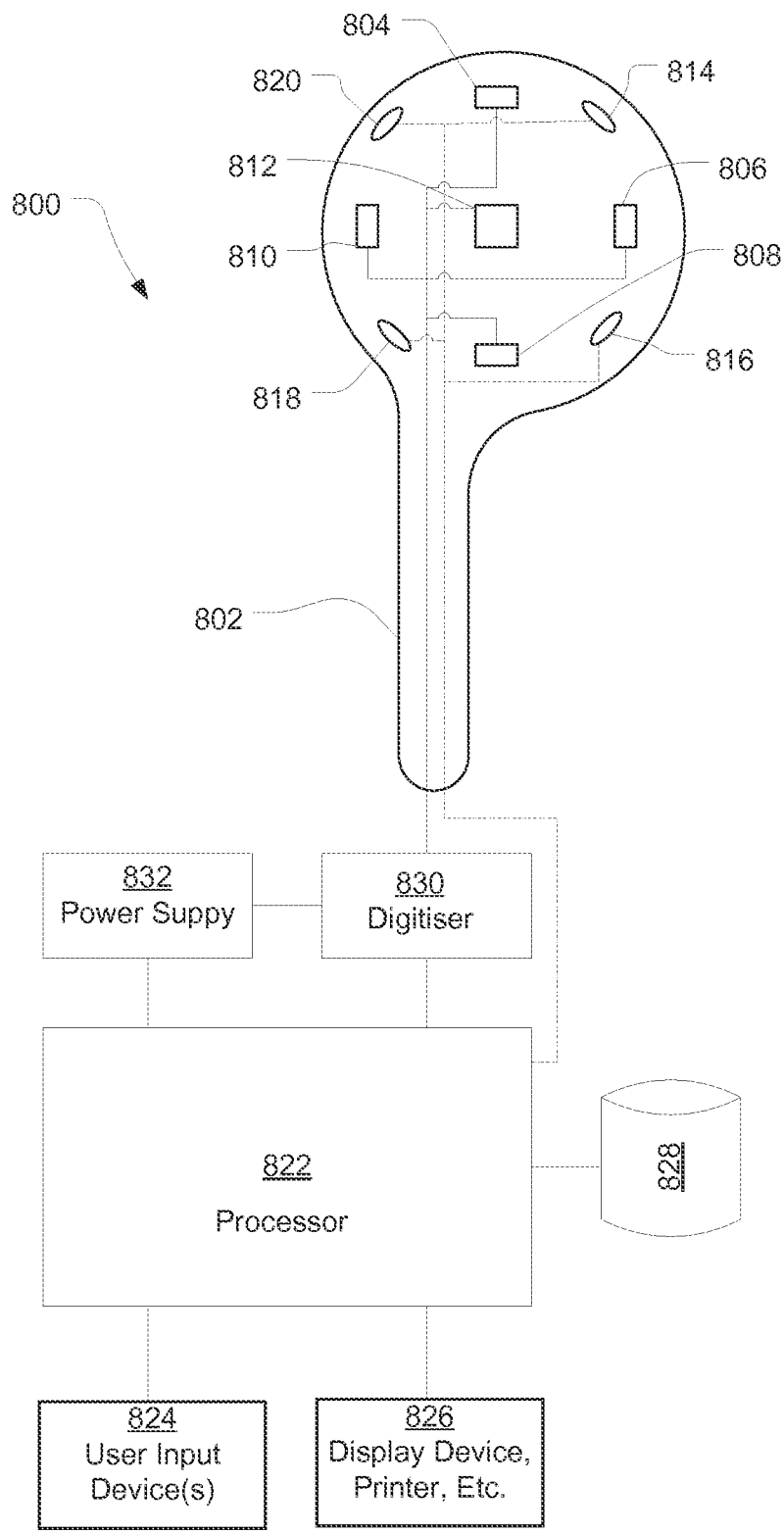
FIG. 8 is a schematic block diagram illustrating components of a system for measuring skin flap thickness, d, for an implanted medical device, according to another embodiment of the present technology.

FIG. 8 illustrates a system 800 for measuring the skin flap thickness, d, of an implanted medical device, according to another embodiment of the present technology. In other words, the system determines the depth of the coil 502 of the implanted device 500. This can be done, e.g., by measuring the distance to the magnetic element that is in a fixed physical relationship with the coil.

Figure 10:
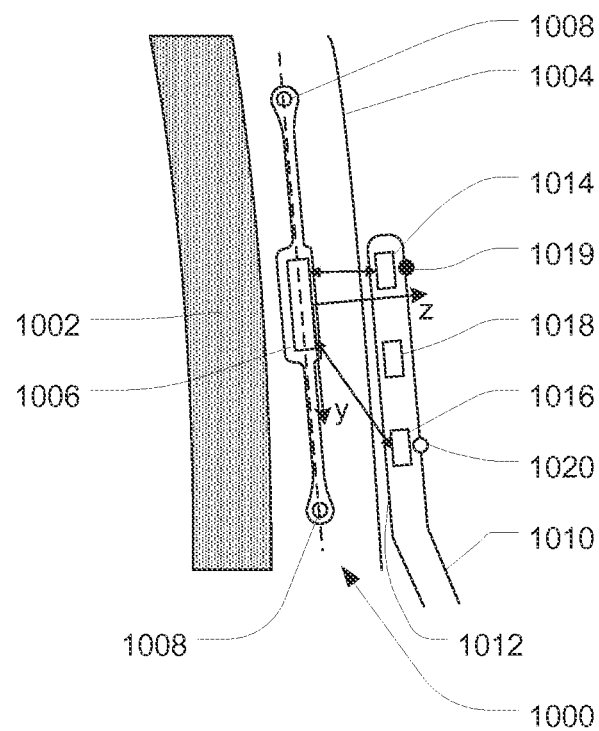
FIG. 10 illustrates an initial step in aligning a probe of the system FIG. 8 with the magnetic element of the implanted component of the implantable medical device, according to another embodiment of the present technology.
Figure 11:
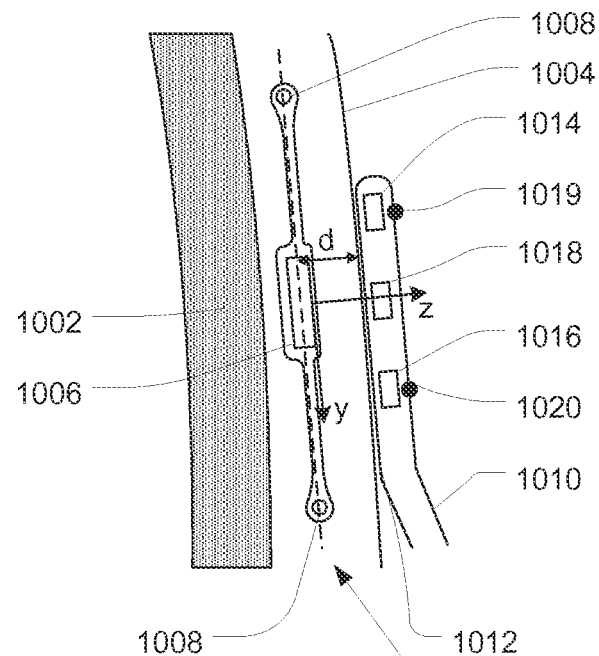
FIG. 11 illustrates a final position of alignment of the probe with the implanted components, in which the skin flap thickness measurement can be made, according to the embodiment of FIG. 10.

The testing system 800 generally comprises a testing wand 802 carrying an array of Hall effect sensors 804 to 812 and an array of indicators 814 to 820. The array of indicators and Hall effect sensors are connected via respective wiring to other components of the analysis system, as described below. The analysis system 800 additionally includes a processor 822 which controls the operation of the system 800 and runs suitable software for analysing the output of the Hall effect sensors of the testing wand 802. Memory system 828 is also provided. The memory system 828 includes memory for carrying machine readable instructions for controlling the operation of the processor 822 and additionally includes a data storage system for storing results from testing and other data as required. The memory system 828 also stores a model of the expected magnetic field produced by the magnetic element of a device under test. This can be, e.g., in the form of a look up table of expected Hall effect sensor outputs induced by the modelled magnetic field at a plurality of locations. These location specific magnetic field data can be arranged in groups corresponding to the specific separation and relative spatial positioning of the hall effect sensors in the testing wand 802. The model may be simplified if it is assumed that the orientation of the wand will be aligned in a particular orientation with respect to the magnetic element being detected. In this example, as illustrated in FIGS. 10 and 11, the wand 802 is assumed to be parallel to the skin surface and consequently parallel to the plane of the magnetic element 508.

The system 800 also includes one or more user input devices 824 for entering data into the system and display, printer or other output devices 826 for providing feedback and data back to a user of the system.

The system 800 additionally includes a digitiser 830, e.g., an analog-to-digital converter. The digitiser 830 samples the time varying output of the Hall effect sensors 804 to 812.

Each of the components of the system is powered by a power supply 832. As described in connection with FIG. 3 the power supply 832, e.g., is a battery, or if supplied from the electrical mains is arranged to comply with power supply requirements for medical devices to ensure patient and operator safety. Similarly, one possible embodiment of the system 800 is to incorporate all of the components of the system 800 into the casing of the wand 802.

In use, the testing wand 802 is placed adjacent the site of the implantation of an implantable device 500 and the Hall effect sensors 804 to 812 interact with, and sense, the magnetic field produced by the magnetic element 508 of the implantable unit 500. The digitised outputs from the Hall effect sensors are provided to the processor 822 which compares the plurality of Hall effect sensor values to its stored model of the expected magnetic field of the magnetic element 508. The model of the expected magnetic field can be expressed, e.g., as a lookup table of expected Hall effect sensor readings for the plurality of sets of positions around the magnetic element 508.

The processor 822 compares the Hall effect sensor outputs with data in the model and determines a spatial position that corresponds to the Hall effect sensor outputs. Thereby the processor 822 is able to determine the location of the wand 802 relative to the magnetic element 508. It will be appreciated that, because the magnetic field of the magnetic element 508 drops away rapidly with distance between the Hall effect sensor and the magnetic element, it will generally be advantageous to accurately position the wand 802 with respect to the magnetic element 508 prior to attempting to determine the implantation depth d of the magnetic element 508.

In order to do assist in alignment of the wand 802, the Hall effect sensor readings can initially be used to determine an approximate position of the wand with respect to the magnetic element 508 by comparing the Hall effect sensor readings to the stored model of the magnetic field of the magnetic element 508. The wand 802, as noted above, is provided with a set of indicators 814 to 820, for example which may be LEDs or similar indicia that can be selectively activated by the processor 822 to indicate to the user of the system 800 a direction to move the wand 802, to more closely align the Hall effect sensors with the magnetic element 508.

As can be seen in FIG. 8, the Hall effect sensors 804 to 812 are arranged, e.g., in a cross pattern with four outer Hall effect sensors 804 to 810 located at the ends of the arms of the cross and a central Hall effect sensor 812 at the centre of the cross. In use, the processor 822 can be programmed to either use the central Hall effect sensor 812 solely for the distance calculation to the magnetic element, once correct alignment has been achieved using the external Hall effect sensors 804 to 810. Alternatively, the depth measurement can be biased to more heavily weight a distance d determined according to the central Hall effect sensor 812. Other schemes, e.g. which equally use all sensors, can be used. Which approach is optimal will depend on the configuration of the magnetic field produced by the magnetic element being located.

The present example includes 5 Hall effect sensors 804 to 812, but this number is not fixed. Other examples may include more or fewer sensors, or sensors of a different type. A single sensor could be used, but more precise alignment becomes more important. Alternatively, a single sensor could be swept across a region to determine the magnetic field at a plurality of known positions along the swept path.

Figure 9:
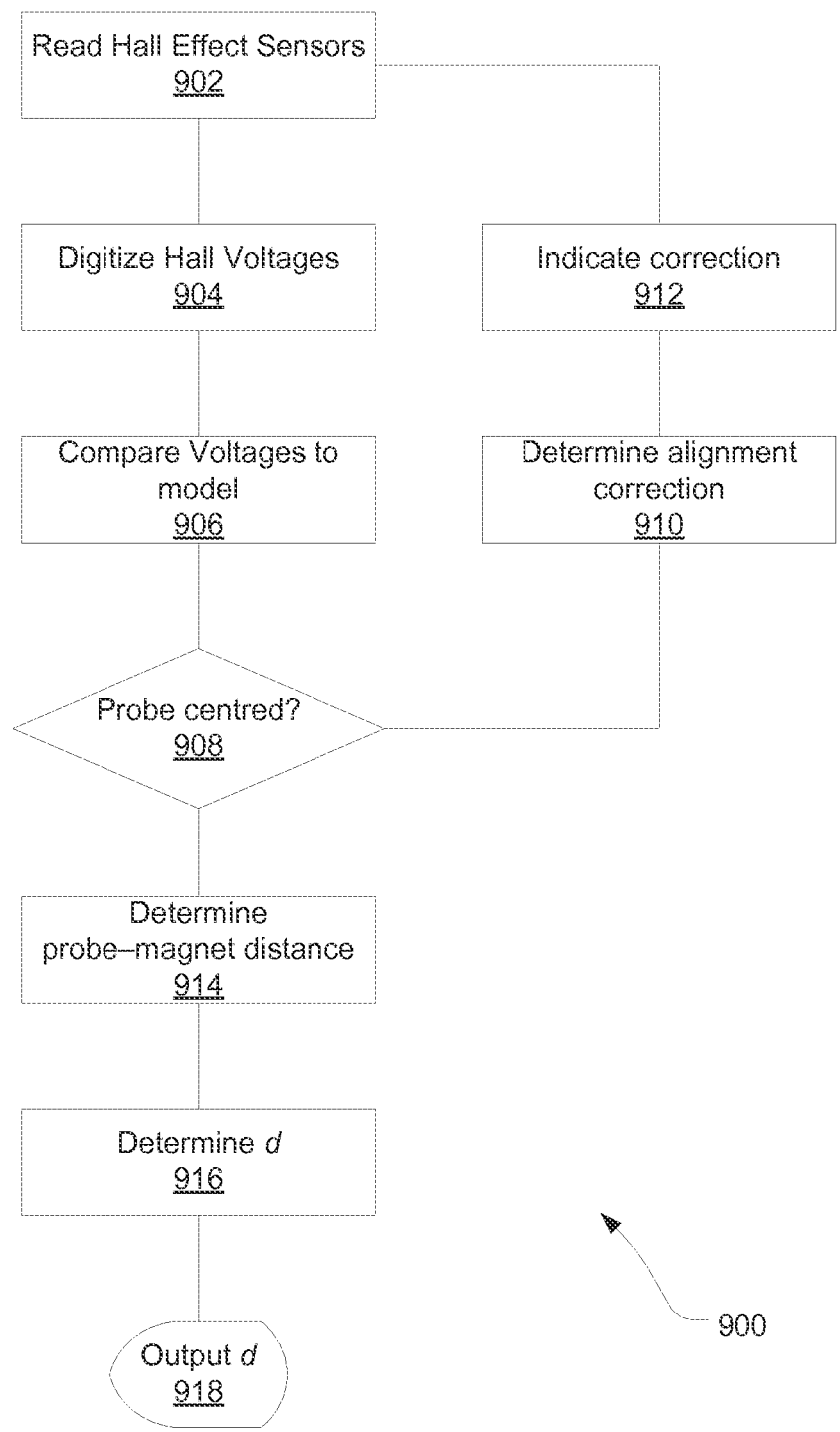
FIG. 9 is a flowchart illustrating a method, according to another embodiment of the present technology, for using the system of FIG. 8 to measure skin flap thickness.

Turning now to FIG. 9, it illustrates a method of using a system of the type illustrated in FIG. 8, according to another embodiment of the present technology. The method 900 begins after a user has activated the system 800 and placed the wand 802 such that its Hall effect sensors 804 to 812 are roughly aligned with the magnetic element 508 of the recipient's implanted device.

In block 902, the outputs of the Hall effect sensors 804 to 812 are read and passed to the digitiser 830 at block 904 which outputs a digital signal indicating the Hall effect voltage at each Hall effect sensor 804 to 812 at a particular point in time. The set of Hall effect sensor voltages is compared to the voltages from the magnetic field model and a relative position of the wand 802 and magnetic element 508 is determined at block 906. Details of block 906 are provided, e.g., via FIGS. 13 and 14.

Figure 13:
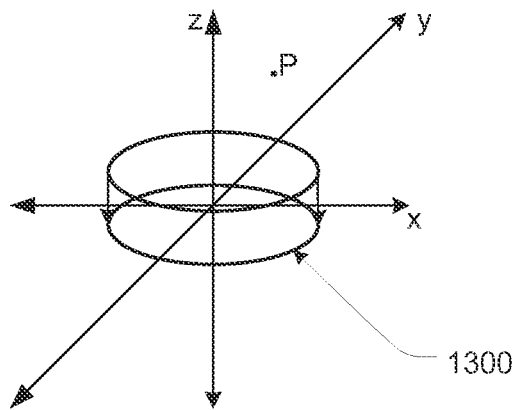
FIG. 13 illustrates a magnetic element that forms part of an implantable unit of a medical device, according to another embodiment of the present technology.
Figure 14:
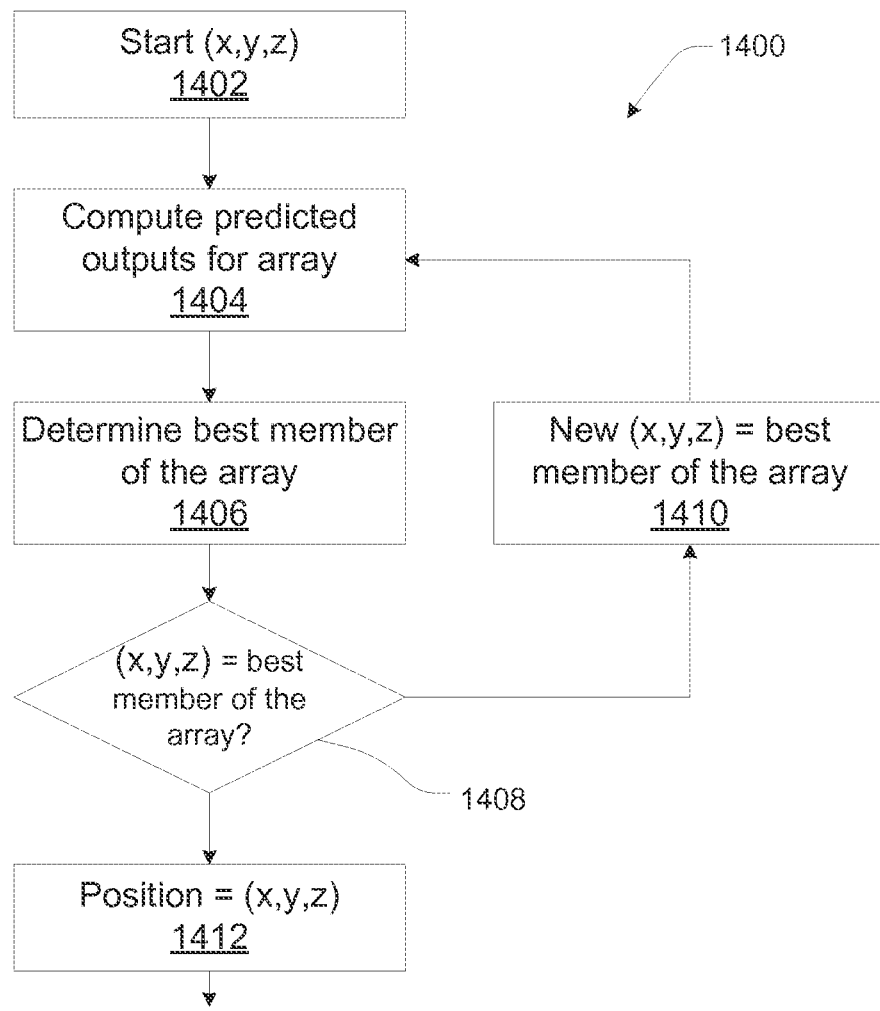
FIG. 14 is a flowchart illustrating a method, according to another embodiment of the present technology; of comparing sensed magnetic field measurements with a magnetic field model as used in an embodiment.

FIGS. 13 and 14 describe an exemplary process for using a magnetic model to determine the position of magnetic field sensing device relative to a magnetic element of an implanted medical device. This process is based on the knowledge that given the shape of a magnetic element and the magnetic properties of the material of the magnetic element, the magnetic field in the space surrounding the magnetic element can be computed. Therefore it is possible to determine what magnetic field should be experienced by a magnetic field sensor when it is placed in the vicinity of the magnet. Consequently the outputs produced by a magnetic field sensor can be predicted for any position of the sensor.

FIG. 13 illustrates an example of a magnetic element 1300 that might be used in an implantable device. In FIG. 13, magnetic element 1300 is illustrated as a cylindrical magnet, the poles of magnet which are aligned along the Z axis. Using the known properties of magnetic fields, it is possible to compute the magnetic field at any point P.

FIG. 14 illustrates a method 1400, according to another embodiment of the present technology, for determining a position of a magnetic element, e.g., 1300, of an implanted device relative to the magnetic field testing wand 802 of FIG. 8.

Once the wand 802 is brought into relatively close proximity to the magnetic element 1300, a set of suitable outputs from the Hall effect sensors 804 to 812 within the wand 802 are produced, and the method 1400 of FIG. 14 is used to determine the relative position of the wand 802 with respect to the magnetic element 1300 as follows. Initially at block 1402, an initial starting position (x,y,z) for the wand 802 relative to the magnetic element 1300 is nominated. This can be, e.g., a random selection, a selection at the origin of the coordinate system, an ideal position or some other selection. Next, in block 1404, the expected Hall effect voltages at position (x,y,z) and an array of nearby positions are computed. In this example, a Cartesian grid of 3×3×3 positions, centred on (x,y,z) is used, resulting in 27 positions, with 27 corresponding expected hall effect voltages.

Next in block 406, the error between each of the 27 computed Hall effect voltages and each of the 5 sensed hall effect voltages from the Hall effect sensors 804 to 812 is computed. For each position in the array of positions, a total error is calculated, e.g., using the sum of the squared error for each sensed Hall effect voltage, i.e., using 27 total error values. Once the total error is calculated for all 27 positions, the position within the array of positions with the best (minimum) error is identified.

Next in block 1408, the best position in the array of positions is compared to the current value of (x,y,z).

If the position amongst the array of 27 positions with the smallest error is the current (x,y,z), then (x,y,z) is determined to be the position of the wand 802 with respect to the magnetic element 1300, in block 1412. Otherwise, in block 1410, the position which gave the smallest error is used as a new (x,y,z). This process is then iterated until the current position estimate (x,y,z) provides the best position estimate. The process can also be iterated starting with a relatively coarsely spaced array of points in block 1404, and subsequently using a successively finer array at each iteration until a desired degree of spatial resolution is attained.

The process of searching for the estimated position of the magnetic element can be made faster by pre-computing the expected Hall effect voltages for every position in a pre-selected grid around the magnet element 1300 and storing these voltages in a lookup table. For example, a grid could contain expected hall effect voltages for each position at every x and y coordinate between −10 mm and +10 mm in 0.25 mm increments and for every z coordinate between 2 mm and 20 mm in 0.1 mm blocks. This would result in a table having 1187541 sets of expected Hall effect voltages.

Other methods of finding an estimate of the magnetic element position are possible. The process described above could be thought of as finding the value of a function (x,y,z)=P({V}) where {V} is the measured set of Hall effect voltages. A suitably precise mathematical expression for this function can be used to model the magnetic field of the magnetic element, e.g., by fitting an algebraic function to the values predicted by the model. This fitted function can then be used to directly estimate the magnet position given a set of Hall voltages.

Returning now to FIG. 9, if the comparison at block 906 reveals that the determined position (x,y,z) (e.g. see block 1412 of FIG. 14) indicates a separation greater than a particular threshold, then at block 908, it is determined that the wand 802 is not sufficiently well aligned with the magnetic element of the recipient's implanted device. In this case, at block 910, the processor 822 makes a determination of a preferred direction of movement of the wand 802 with respect to the magnetic element, and one or more of the indicators 814 to 820 on the wand 802 is illuminated, in block 912, to tell the user of the device which direction to move the wand 802 to better align it with the magnetic element of the implanted medical device.

In the event that the wand 802 is determined to be sufficiently aligned, e.g. the x and y positions indicate that the wand 806 is aligned with the z axis of the magnetic element 508, a final distance between the magnetic element and wand 802 is determined at block 914. The distance determined in block 914, may need to be corrected for any offset in implant depth between the magnetic element and the coil of the implanted medical device (given that the position of the coil is the important factor for coupling efficiency of the wireless transmission link), or any offset between the Hall effect sensor positions and the external surface of the wand 802 which contacts the recipient's skin during test. If correction for these two dimensions is required, this is performed in block 916 and the skin thickness d is outputted in block 918.

As will be appreciated the alignment process described herein can also tell the user the lateral position of the magnetic element 1006 and by extension the lateral position of the device 1008 to which it is attached; see FIGS. 10-11.

FIGS. 10 and 11 together serve to illustrate a concept of aligning the probe with the magnetic element prior to final determination of skin flap thickness, according to another embodiment of the present technology. In this regard FIG. 10 illustrates a similar view to that of FIG. 7 and illustrates an implanted medical device 1000 positioned between a bone 1002 and skin surface 1004. The medical device 1000 includes a magnetic element 1006 which is located in a fixed physical relationship with a coil 1008 of the wireless electrical transmission system of the medical device. In order to test the skin flap thickness, the probe 1010 is brought such that its lower side 1012 contacts the skin surface 1004.

In this example, a Cartesian coordinate system is used, having its origin in the centre of the outermost surface of the magnetic element 1006. The outermost surface of the magnetic element lies in the x-y plane of the coordinate system and the z axis extends outward, in a direction normal to the outermost surface of the magnetic element 1006. The illustration is a cross section along the y-z plane.

In this cross-sectional view, three Hall effect sensors 1014, 1016 and 1018 can be seen. As will be appreciated, the distance between the magnetic element 1006 and Hall effect sensor 1014 is substantially shorter than the distance between the magnetic element 1006 and Hall effect sensor 1016 and accordingly, the magnetic field perceived by the Hall effect sensor 1014 will be far greater than that perceived by the Hall effect sensor 1016. When the outputs of the Hall effect sensors 1014-1018 are compared with the stored model, the model will indicate that the final determined position (x,y,z) of the set of Hall effect sensors 1014, 1016 and 1018 is not sufficiently aligned with the centre of the magnetic element 1006 and therefore that the probe 1010 needs to be moved upward to more correctly align the central Hall effect sensor 1018 with the centre of the magnetic element 1006. The alignment of the probe 1010 with the magnetic element 1006 is determined by comparing the x and y positions of the probe with those expected for correct alignment, e.g., ((0,0) with this presently defined origin of the coordinate system). In the event that they are not the same (or not sufficiently similar), the offset direction can be determined. In order to convey the necessary direction of movement to reduce the computed offset to the user of the probe 1010, indicator light 1019 is illuminated whereas indicator light 1020 is left un-illuminated—indicating that the user should move the probe in the y direction, towards the direction of the illuminated indicator light 1019. Thus, the user is told which direction to move the sensor probe 1010.

Due to the speed of processing and comparing the magnetic fields with the model, this alignment process can be performed repeatedly, and can be used to steer the alignment of the probe 1010 in real time. FIG. 11 illustrates the arrangement of FIG. 10 but with the probe 1010 correctly aligned such that the central Hall effect sensor 1018 is aligned with the centre of the magnetic element 1006. Once correct alignment has been established such as in FIG. 11, the z coordinate determined by use of the magnetic field model is used to determine the distance d, being the implantation depth of the coil 1008. Correct alignment is indicated to the user, e.g. by illuminating all indicia on the wand. The user can then choose to accept the current distance d, e.g. by pressing a button on the wand or through some other input.

As will be appreciated, this embodiment of the present technology can be used to measure the implantation depth to any implanted component of a medical device that is in a known physical relationship with a magnetic element.

In the context of measuring the implantation depth of a coil forming part of a wireless transmission link in the implanted component of a medical device, knowledge of implantation depth can be very useful. For surgeons, a knowledge of implantation depth can be used to hone their implantation technique so that optimum implantation dept can be achieved. Moreover, regular checking of implantation depth following implantation can be used to check swelling around the implantation site.

Figure 12:
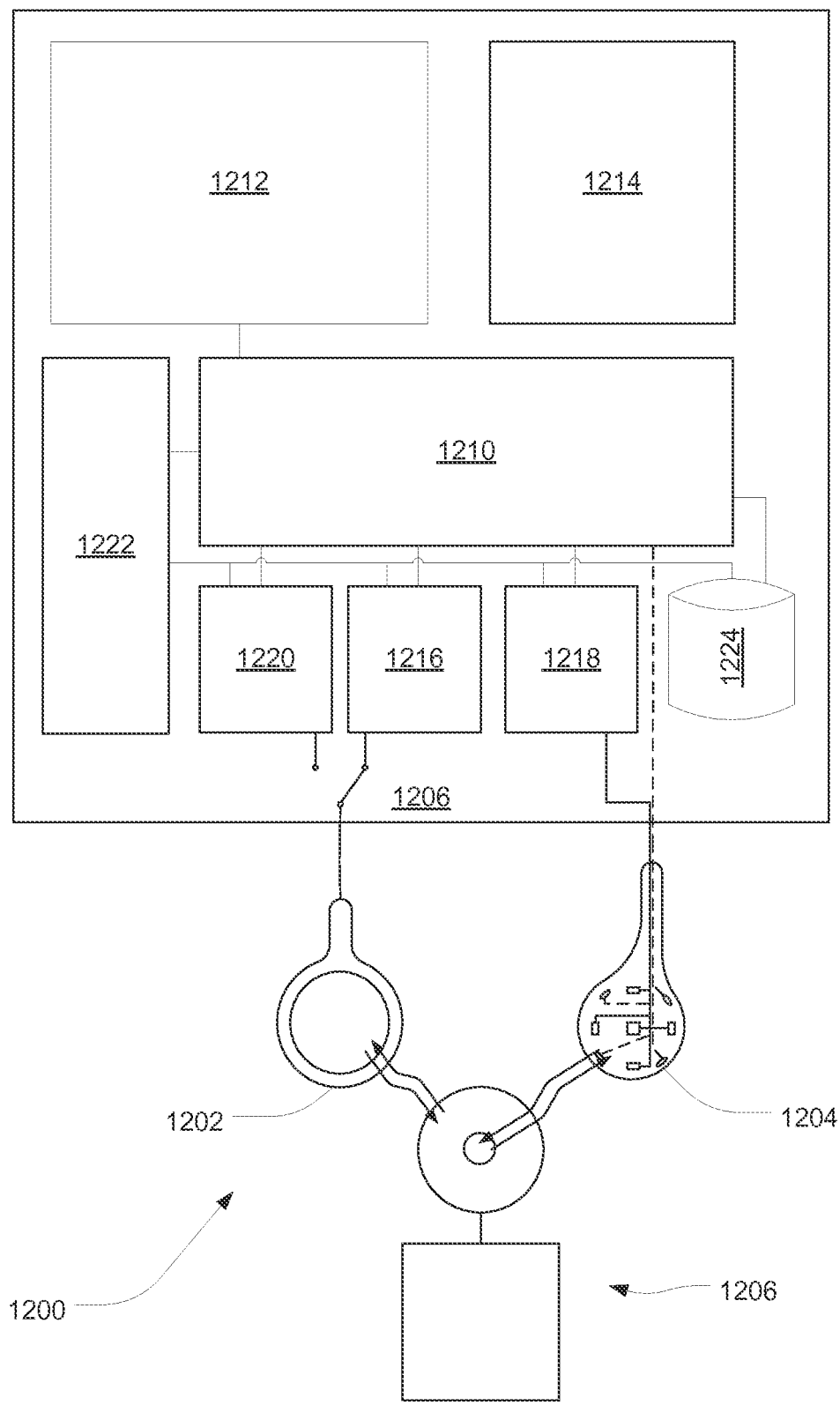
FIG. 12 illustrates a system for measuring the properties of the tuned circuit of an implanted medical device and skin flap thickness, according to another embodiment of the present technology.

FIG. 12 illustrates a further system made in accordance with an embodiment of the present technology. The system at FIG. 12 performs the functions of the two systems of FIGS. 3 and 8. The system 1200 includes a pair of probes 1202 and 1204 which are electrically connected to a test unit 1206. The probe 1202 is used for testing the parameters of the tuned circuit of the device under test 1206 as described in connection with FIGS. 3 and 4. The probe 1204 is similar to the probe illustrated in FIG. 8 and is used to determine the skin flap thickness. The measurement unit 1206 includes a processing system 1210 which runs suitable software to control the operation of the device and communicate its output with a display 1212. As will be appreciated the circuit testing functionality requires digitisation of a signal oscillating at around 5 MHz whereas the outputs from the Hall effect sensors of the probe 1204 will produce a much lower frequency signal and thus only require a lower speed A/D converter. Accordingly, inputs from the probes 1204 and 1206 provided to the processor via a high speed and low speed analogue digital converters 1216 and 1218 respectively. The high speed A/D converter is connected to the circuit testing probe 1202 and the low speed A/D converter 1218 is connected to the skin flap thickness testing probe 1204.

The system 1206 additionally includes a signal generator 1220 for providing a radio frequency signal to the circuit testing probe 1202. All components of the system 1206 are powered by a power supply 1222 and memory requirements for the processing system are handled by a memory system 1224.

The system also includes a power supply and input and output devices, analogous to those described in earlier embodiments.

In use the system of FIG. 12 can be used to determine the location of an implanted component of an implantable medical device in the manner described above. Similarly the system of FIG. 12 can be used to test a property of a tuned circuit, e.g. a tuned circuit forming part of a wireless energy or data transmission system of the device, in the manner described above.

The invention described and claimed herein is not to be limited in scope by the specific example embodiments herein disclosed, since these embodiments are intended as illustrations, and not limitations, of several aspects of the present invention. Any equivalent embodiments are intended to be within the scope of the present invention. Indeed, various modifications of the present invention in addition to those shown and described herein will become apparent to those skilled in the art from the foregoing description. Such modifications are also intended to fall within the scope of the appended claims.

What is claimed is:

1. A method of testing an implantable medical device, the implantable medical device including a tuned circuit having a coil for transferring energy between the implantable medical device and another device, the method comprising:
   inducing, with a signal generator and a test coil connected to the signal generator, an EMF in the coil of the tuned circuit;
   disconnecting the signal generator from the test coil;
   selectively connecting the test coil to a digitizer;
   detecting, with the test coil and the digitizer, a resonance of the tuned circuit in response to the EMF induced in the coil of the tuned circuit; and
   analyzing the detected resonance over a period of time to determine a property of the tuned circuit.

2. The method of claim 1, wherein the inducing the EMF includes:
   applying a time varying magnetic field to the coil of the tuned circuit.

3. The method of claim 2, wherein the inducing the EMF includes:
   applying the time varying magnetic field for at least an amount of time sufficient for the tuned circuit of the implantable medical device to reach a threshold state, prior to detecting a resonance of the tuned circuit.

4. The method of claim 1, wherein the analyzing includes:
   determining a quality factor (Q) of the tuned circuit as the property thereof.

5. The method of claim 1, wherein the analyzing includes:
   determining at least one resonant frequency of the tuned circuit as the property thereof.

6. The method of claim 1, wherein the detecting resonance includes:
   detecting a time varying magnetic field generated by the tuned circuit.

7. The method of claim 6, wherein the analyzing includes:
generating a time varying voltage signal in response to the time varying magnetic field; and
sampling the time varying voltage signal over a sampling interval to generate instantaneous voltage samples at corresponding times.

8. The method of claim 7, wherein the analyzing the detected resonance includes:
fitting a curve to the sampled instantaneous voltage values over at least the sampling interval.

9. The method of claim 8, wherein:
the curve fitted to the sampled instantaneous voltage values has a decaying sinusoidal form.

10. The method of claim 8, wherein the curve fitted to the sampled instantaneous voltage values is of the general form:

$$v = Ve^{\frac{t}{\tau}}\sin(2\pi ft + \phi)$$

where,
v is the voltage at time t;
V is an initial voltage amplitude at a start of the measurement window;
τ is a decay constant describing the energy dissipated in a cycle of the received signal compared to the total signal energy;
f is the resonant frequency of the tuned circuit; and
φ is a phase offset.

11. The method of claim 10, wherein the curve fitted to the sampled instantaneous voltage values further includes terms to account for at least one of more of the following:
a predictable unwanted component in the generated time varying voltage signal;
an artefact introduced into the instantaneous voltage samples by the sampling process; and
a distortion caused by the presence of a non-linear component in the tuned circuit.

12. The method of claim 1, wherein:
the method is performed prior to implantation of the implantable medical device.

13. The method of claim 1, wherein:
the method is performed on an implantable medical device in vivo.

14. The method of claim 1, wherein the implantable medical device is an implanted auditory prosthesis.

15. A system for testing an implantable medical device, the implantable medical device including a tuned circuit having a coil for transferring energy between the implantable medical device and another device, the system comprising:
a signal generator configured to induce, via a test coil, an EMF in the coil of the tuned circuit;
a digitizer configured to detect, via the test coil, a resonance of the tuned circuit in response to the EMF induced in the coil of the tuned circuit;
a switch circuit configured to alternatively connect the test coil to the signal generator and the digitizer; and
a processing system configured to analyze the detected resonance over a period of time to determine a property of the tuned circuit.

16. A method of testing an implantable medical device, comprising:
selectively connecting, via a switch, a signal generator of a testing system to a dual-function test coil;
inducing, with the signal generator, an EMF in an implantable coil of a tuned circuit;
selectively connecting the dual-function test coil to a digitizer;
detecting, with the digitizer, a resonance of the tuned circuit in response to the EMF induced in the implantable coil; and
analyzing the detected resonance to determine a property of the tuned circuit.

17. The method of claim 16, wherein the inducing the EMF includes:
applying a time varying magnetic field to the implantable coil.

18. The method of claim 16, wherein the analyzing comprises:
determining a quality factor (Q) of the tuned circuit.

19. The method of claim 16, wherein the analyzing comprises:
determining at least one resonant frequency of the tuned circuit.

20. The method of claim 16, wherein the detecting resonance comprises:
detecting a time varying magnetic field generated by the tuned circuit.

21. The method of claim 20, wherein the analyzing includes:
generating a time varying voltage signal in response to the time varying magnetic field; and
sampling the time varying voltage signal over a sampling interval to generate instantaneous voltage samples at corresponding times.

22. The method of claim 21, wherein the analyzing includes:
fitting a curve to the sampled instantaneous voltage values over at least the sampling interval.

23. The method of claim 16, further comprising:
monitoring an amplitude of the detected resonance to detect an alignment of the dual-function test coil with the implantable coil.

* * * * *